United States Patent
Christensen, Jr.

(10) Patent No.: US 6,534,466 B2
(45) Date of Patent: *Mar. 18, 2003

(54) LOW-DENSITY COMPOSITIONS AND PARTICULATES INCLUDING SAME

(75) Inventor: Robert I. Christensen, Jr., Pinole, CA (US)

(73) Assignee: Genencor International, Inc., Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 158 days.

(21) Appl. No.: 09/479,693

(22) Filed: Jan. 7, 2000

(65) Prior Publication Data

US 2002/0082183 A1 Jun. 27, 2002

Related U.S. Application Data

(60) Provisional application No. 60/115,255, filed on Jan. 8, 1999.

(51) Int. Cl.⁷ ............. C11D 3/00; C11D 7/42; C12S 9/00
(52) U.S. Cl. ............. 510/392; 435/187; 435/179; 435/183
(58) Field of Search ............. 510/392; 435/187, 435/179, 183

(56) References Cited

U.S. PATENT DOCUMENTS

| | | | |
|---|---|---|---|
| 4,106,991 A | | 8/1978 | Markussen et al. |
| 4,689,297 A | | 8/1987 | Good et al. |
| 4,740,469 A | | 4/1988 | Nishinaka et al. |
| 4,760,025 A | | 7/1988 | Estell et al. |
| 4,931,195 A | * | 6/1990 | Cao et al. .................. 252/8.8 |
| 5,324,649 A | * | 6/1994 | Arnold et al. .............. 435/187 |
| 5,739,091 A | | 4/1998 | Kiesser et al. |
| 5,814,501 A | | 9/1998 | Becker et al. |
| 5,846,798 A | * | 12/1998 | Paatz et al. ................. 435/187 |

FOREIGN PATENT DOCUMENTS

| | | |
|---|---|---|
| EP | 0 130 756 B1 | 6/1991 |
| FR | 2 618 157 A1 | 1/1989 |
| JP | 57 188435 A | 11/1982 |
| WO | WO 90/09440 A1 | 8/1990 |
| WO | WO 91/06637 | 5/1991 |
| WO | WO 91/09941 | 7/1991 |
| WO | WO 97/12958 | 4/1997 |
| WO | WO 97/30145 A1 | 8/1997 |
| WO | WO 99/00471 A1 | 1/1999 |
| WO | WO 99/32595 | 7/1999 |
| WO | WO 99/32612 | 7/1999 |
| WO | WO 99/32613 | 7/1999 |
| WO | WO 00/29534 A1 | 5/2000 |

* cited by examiner

Primary Examiner—Yogendra N. Gupta
Assistant Examiner—Eisa Elhilo
(74) Attorney, Agent, or Firm—Genencor International, Inc.

(57) ABSTRACT

The present invention provides low-density compositions, as well as particulates formed, at least in part, from such compositions. Preferred low-density materials include, for example, hollowspheres, low-density minerals, and low-density wood materials (e.g., sawdust). The low-density compositions of the invention can be formed as particulates, or cores, suitable for use in forming enzyme granules, e.g., marums, layered granules, prills, drum granules, agglomerated granules, or the like. Granules are disclosed having advantageous properties, e.g., low dusting, storage stable, fast enzyme-release profile, low true density, etc. The granules of the invention are especially useful, for example, in liquid detergents and cleaners, such as predominantly aqueous, liquid laundry detergents. In one embodiment, granules are provided having a true, or volumetric, density within a range of from about 0.95 to about 1.4 g/cm³. The granules can be economically produced in commercial quantities by way of a marumerization, drum granulation, fluid-bed spray-coating, pan-coating, or other suitable process.

19 Claims, No Drawings

LOW-DENSITY COMPOSITIONS AND PARTICULATES INCLUDING SAME

This application claims priority to U.S. Provisional Application No. 60/115,255, filed Jan. 8, 1999, which is incorporated herein in its entirety.

FIELD OF THE INVENTION

The present invention relates to low-density compositions, as well as particulates formed, at least in part, from such compositions. More particularly, the present invention provides low-density compositions including a non-porous or minimally porous, low-density material. Particulates formed from the low-density compositions of the invention are especially useful as cores for enzyme granules.

BACKGROUND OF THE INVENTION

The use of proteins such as pharmaceutically important proteins, e.g., hormones, and industrially important proteins, e.g., enzymes, has been rapidly growing in recent years. Today, for example, enzymes find frequent use in the starch, dairy, and detergent industries, among others.

In the detergent industry, in particular, enzymes are often configured in a granular form, with an eye toward achieving one or more desirable storage and/or performance characteristics, depending upon the particular application at hand. In these regards, the industry has offered numerous developments in the granulation and coating of enzymes, several of which are exemplified in the following patents and publications:

U.S. Pat. No. 4,106,991 describes an improved formulation of enzyme granules by including within the composition undergoing granulation, finely divided cellulose fibers in an amount of 2–40% w/w based on the dry weight of the whole composition. In addition, this patent describes that waxy substances can be used to coat the particles of the granulate.

U.S. Pat. No. 4,689,297 describes enzyme containing particles which comprise a particulate, water dispersible core which is 150–2,000 microns in its longest dimension, a uniform layer of enzyme around the core particle which amounts to 10%–35% by weight of the weight of the core particle, and a layer of macro-molecular, film-forming, water soluble or dispersible coating agent uniformly surrounding the enzyme layer wherein the combination of enzyme and coating agent is from 25–55% of the weight of the core particle. The core material described in this patent includes clay, a sugar crystal enclosed in layers of corn starch which is coated with a layer of dextrin, agglomerated potato starch, particulate salt, agglomerated trisodium citrate, pan crystallized NaCl flakes, bentonite granules or prills, granules containing bentonite, kaolin and diatomaceous earth or sodium citrate crystals. The film forming material may be a fatty acid ester, an alkoxylated alcohol, a polyvinyl alcohol or an ethoxylated alkylphenol.

U.S. Pat. No. 4,740,469 describes an enzyme granular composition consisting essentially of from 1–35% by weight of an enzyme and from 0.5–30% by weight of a synthetic fibrous material having an average length of from 100–500 micron and a fineness in the range of from 0.05–0.7 denier, with the balance being an extender or filler. The granular composition may further comprise a molten waxy material, such as polyethylene glycol, and optionally a colorant such as titanium dioxide.

U.S. Pat. No. 5,324,649 describes enzyme-containing granules having a core, an enzyme layer and an outer coating layer. The enzyme layer and, optionally, the core and outer coating layer contain a vinyl polymer.

WO 91/09941 describes an enzyme containing preparation whereby at least 50% of the enzymatic activity is present in the preparation as enzyme crystals. The preparation can be either a slurry or a granulate.

WO 97/12958 discloses a microgranular enzyme composition. The granules are made by fluid-bed agglomeration which results in granules with numerous carrier or seed particles coated with enzyme and bound together by a binder.

Notwithstanding such developments, there is a continuing need for enzyme granules which have additional beneficial or improved characteristics. For example, while enzyme granules for dry (e.g., powdered) detergent formulations have become widely known and extensively developed (as exemplified above), few, if any, granule formulations are available which are suitable for incorporation in liquid detergents.

In some respects, formulators of enzyme granules for liquid detergents must address concerns much like those encountered with dry detergent formulations. It should be appreciated, however, that a liquid-detergent environment presents a variety of challenges of its own. Some of these considerations are discussed next.

In both liquid and dry detergent formulations, enzyme granules should be capable of providing sufficient enzyme activity in the wash. It is also generally desirable to have granule with a relatively fast release profile. Thus, the enzyme load for each granule needs to be protected from the various harsh components of the liquid formulation (e.g., peroxygen bleaches, such as sodium perborate or sodium percarbonate, and the like), yet the means of achieving such protection must not unduly hinder enzyme release. As is well known by those working in the field, it is often problematic to simultaneously provide good protection for the enzyme and a fast release profile.

Another concern, which is common to most all enzyme granules, relates to attrition resistance. In today's state of ever-increasing environmental concern and heightened awareness of industrial hygiene, it is important to keep enzyme dust within acceptable levels. It should be appreciated that human contact with airborne enzyme dust can cause severe allergic reactions. For these reasons, enzyme granule formulators continue their endeavors to control (reduce) the susceptibility of enzyme granules to attritional breakdown.

With particular regard to liquid detergent formulations, one problem with the use of particles (which would include enzyme granules) in liquids is that there is a tendency for such products to phase separate as dispersed insoluble solid particulate material drops from suspension and settles at the bottom of the container holding the liquid detergent product. Phase stabilizers such as thickeners or viscosity control agents can be added to such products to enhance the physical stability thereof. Such materials, however, can add cost and bulk to the product without contributing to the laundering/ cleaning performance of such detergent compositions. Further, it is to be noted that the known enzyme granules are generally unsuitable for use in typical liquid detergents as such granules generally have an unacceptably high density (e.g., 1.45 g/cm$^3$, or higher) which would cause them to drop out of suspension in a relativity short period of time (i.e., much less than the typical product shelf life).

A further problem associated with particles in liquids is that it has been observed that the particles can induce visual inhomogeneities in the final product. This represents a problem, as composition aesthetics is a key element in terms of consumer acceptance.

In view of the above, the development of a low-density, enzyme-containing granule is needed in order to provide cleaning benefit for liquid detergents. The low density is desired so that the particles will stay suspended in the detergent throughout the intended lifecycle of the product. Additionally, it is desired to have the enzymes protected from the harsh detergent environment so that they remain active throughout the product lifecycle. It is also desirable to have a relatively fast enzyme release profile.

It is therefore an advantage of the present invention to provide low-density particulate compositions and enzyme granules suitable for use in liquid-detergent or cleaner compositions. Preferred particulate compositions and granules of the present invention are characterized by one or more of the following desirable features: they have a true density less than 1.4 g/cm$^3$; they exhibit sufficient enzyme activity in the wash; they have a relatively fast enzyme-release profile; they have relatively low susceptibility to attritional breakdown; they tend to remain dispersed and suspended in the liquid detergent or cleaner during storage and use (e.g., for at least 3 weeks, and preferably for at least 4 weeks); they have sufficient retained activity in storage; they provide an acceptable (pleasing) visual appearance.

The production of such a granule exhibiting two or more of the above features has been especially challenging to the industry. For example, the industry is in need of enzyme particulates and granules for liquid detergents that have a low true density (e.g., less than 1.4 g/cm$^3$, and preferably less than about 1.2 g/cm$^3$), a low susceptibility to attritional breakdown (e.g., no greater than 1.0 ug/g ), and retained activity in storage (e.g., greater than 50%). Moreover, an especially desirable granule would additionally disintegrate quickly in the wash liquor to release its enzyme activity. It is an advantage of the present invention to provide granules meeting such specifications.

It is still a further advantage of the present invention to provide low-density enzyme granules that can be made economically and in commercial quantities. To this end, the present invention provides exemplary methods of producing such granules, e.g., by way of a marumerization, drum granulation, fluid-bed spray coating, pan-coating process, or other suitable process.

SUMMARY OF THE INVENTION

One aspect of the present invention provides a low-density composition including a non-porous or minimally porous, low-density material (e.g., hollowspheres, low-density minerals that are minimally soluble and minimally porous in water, low-density wood materials, or any mixture thereof), a binder or binder system (e.g., sucrose), and one or more enzymes (e.g., a hydrolytic enzyme, such as a protease, amylase, cellulase, lipase, esterases and/or peptidase).

In one embodiment of the invention, the non-porous or minimally porous, low-density material is comprised of hollowspheres (e.g., borosilicate glass hollowspheres, fused glass hollowspheres, ceramic hollowspheres, plastic hollowspheres, or the like). One particularly preferred type of hollowsphere is available commercially under the tradename Q-cel, from PQ Corporation.

Preferably, the low-density composition of the invention has a specific gravity of no greater than about 1.4 g/cm$^3$; and more preferably no greater than about 1.2 g/cm$^3$ (e.g., within a range of between 0.95 and 1.15 g/cm$^3$).

Another aspect of the present invention provides an enzyme-carrying core for enzyme granules. According to one embodiment, the enzyme-carrying core comprises (i) a low-density composition including (a) a non-porous or minimally porous, low-density material and (b) a binder or binder system; and (ii) an enzyme enrobing said composition.

In one embodiment of the enzyme-carrying core, the non-porous or minimally porous, low-density material is selected from the group consisting of hollowspheres, low-density minerals that are minimally soluble and minimally porous in water, low-density wood materials, and any mixture thereof. According to one preferred embodiment, the non-porous or minimally porous, low-density material is comprised of hollowspheres (e.g., Q-cel, from PQ Corporation).

The enzyme-carrying core of the invention can be substantially free of enzymes therein (i.e., it can be a non-enzyme containing core); or the core can contain one or more enzymes. In one embodiment, the core is a non-enzyme containing core, which can be coated with one or more enzymes, as desired.

Preferably, the enzyme-carrying core of the invention has a specific gravity of no greater than about 1.4 g/cm$^3$, and more preferably no greater than about 1.2 g/cm$^3$ (within a range of between 0.95 and 1.15 g/cm$^3$).

In another of its aspects, the present invention provides a low-density enzyme granule. In one embodiment, the granule comprises: (i) a core formed of a low-density composition including a non-porous or minimally porous, low-density material; (ii) one or more enzymes; and (iii) an outer coating.

According to one embodiment, the non-porous or minimally porous, low-density material is selected from the group consisting of hollowspheres, low-density minerals that are minimally soluble and minimally porous in water, low-density wood materials, and any mixture thereof. In a preferred embodiment, the non-porous or minimally porous, low-density material is comprised of hollowspheres (e.g., borosilicate glass hollowspheres).

Preferably, the granules of the present invention have a specific gravity of less than 1.4 g/cm$^3$. In one embodiment, the granules have a specific gravity of no greater than about 1.2 g/cm$^3$ (e.g., within a range of between about 0.95 and 1.15 g/cm$^3$).

Still a further aspect of the present invention provides a method for making a low-density granule. In one embodiment, for example, the method includes the steps of:

c) preparing a well-mixed blend of components, including (i) one or more enzymes, (ii) a non-porous or minimally porous, low-density material, and (iii) a binder; and d) granulating the blend into discreet particulates.

As an additional step, the method can further involve overcoating the particulates with a cosmetic coating (e.g., HPMC, PEG, and TiO$_2$).

In another embodiment, granules of the present invention are formed by carrying out the steps of:

a) selecting a seed or carrier particle;

b) coating the seed with a low-density composition including a non-porous or minimally porous, low-density material;

c) coating the low density composition with one or more enzymes; and d) overcoating with a cosmetic coating.

The non-porous or minimally porous, low-density material is preferably selected from the group consisting of hollowspheres, low-density minerals that are minimally soluble and minimally porous in water, low-density wood materials, and any mixture thereof. In one preferred embodiment, the low-density material is comprised of hollowspheres (e.g., Q-cel, from PQ Corporation).

These and other features, aspects and advantages of the present invention will become apparent from the following detailed description and examples, in conjunction with the appended claims.

DETAILED DESCRIPTION OF THE INVENTION

The present invention provides low-density compositions, as well as particulates formed, at least in part, from such compositions. The low-density compositions of the invention include, at least in part, a non-porous or minimally porous, low-density material. Particulates formed from the low-density compositions of the invention are especially useful as cores for enzyme granules (e.g., marums, layered granules, prills, drum granules, agglomerated granules, or the like). In this regard, the compositions can further include one or more proteins, e.g., hydrolytic enzymes; and/or the compositions, or particulates formed therefrom, can be enrobed with such proteins. The advantage in using the low-density material (also referred to as a bulking agent), is that particulates, cores and granules with densities much lower than those achievable by prior methods can be produced. This can have a bearing on a number of applications, such as dispersion of a suspended particle in a liquid, flotation or buoyancy control of particles in specialized applications (i.e. chromatographic columns), segregation manipulation in powder applications, etc.

As used herein, the term "density" refers to "true density," "specific gravity" or "volumetric density," as opposed to "bulk density" (unless otherwise stated). The former can be determined, for example, by volume displacement using a liquid in which the particulates or granules do not dissolve (e.g., by way of mineral oil immersion).

Generally, according to one embodiment, a low-density composition of the present invention includes a non-porous or minimally porous (e.g., less than 0.25 by water vapor porosity test; preferably less than 0.20; most preferably less than 0. 10), low-density material, e.g., hollowspheres, low-density minerals, low-density wood materials, or any combination thereof, and a binder material. Optionally, one or more proteins, such as an enzyme, can further be included in the low-density composition. The composition can be configured, for example, as a particulate. Where the particulates are intended for use in liquid wash solutions, they are preferably adapted to be readily soluble or dispersable in the wash liquor.

In situations where the product desired is a low-density granule, such particulates can be used as cores, upon which one or more layers can be applied. For example, one or more of the following layers can be applied to a particulate, or core, of the present invention: (i) an enzyme layer surrounding the core (especially where non-enzyme containing particulates are utilized); (ii) optionally, a barrier layer for guarding the enzyme(s) against potentially inactivating substances and/or preventing enzyme leakage; and (iii) an outermost layer, e.g., a protective or aesthetic overcoat. For granules used in detergents, the outermost layer provides a barrier to the harsh detergent elements as well as gives the desired aesthetic properties to the granule.

In exemplary granules of the present invention, the non-porous or minimally porous, low-density material amount is preferably about 1–20% (w/w, relative to the weight of the granule); the enzyme amount is preferably about 0.5–30% (w/w, relative to the weight of the granule); and the outer coating amount is preferably about 1–50% (w/w, relative to the weight of the granule).

Preferably, the low-density material is non-porous or minimally porous in water, substantially non-reactive, and has a low bulk density (e.g., less than 1 g/ml, and preferably no greater than 0.6 g/ml). Preferred low-density materials include, for example, hollowspheres, low-density minerals that are minimally soluble and minimally porous in water, and low-density wood materials. Suitable hollowspheres include, for example, borosilicate glass hollowspheres, fused glass hollowspheres, ceramic hollowspheres and plastic hollowspheres. One particularly preferred type of hollowsphere is available commercially under the tradename Q-cel, from PQ Corporation. Exemplary low-density minerals include aluminum palmitate, aluminum tri-stearate, lithium borohydrate, and potassium borohydride, among others. Suitable low-density wood materials include, for example, saw dust, such as from balsa wood.

Other, optional, low-density materials that may be included in the low-density composition include, for example, fumed silica, low density forms of zeolites (such as used for molecular sieving), low density forms of silicates (such as sodium aluminosilicates used as flow aids for powders), low density forms of silicon dioxide (such as those used as flow aids for powders), milled corncob, aerogel shards, hollow fibers (e.g., Dacron (DuPont)), among others. As previously mentioned, it is preferred herein that the low-density composition of the invention should include at least one non-porous or minimally porous low-density material. Thus, if a generally porous low-density material is used, it is preferred that one or more non-porous or minimally porous materials are also employed.

In one embodiment, the low-density composition of the invention is formed into a particulate, or core, about a small seed or carrier particle. A seed or carrier particle is an inert particle upon which the low-density material (along with a binder and, optionally, one or enzymes) can be deposited (e.g., coated, layered, etc.). Suitable seed particles include inorganic salts, sugars, sugar alcohols, small organic molecules such as organic acids or salts, minerals such as clays or silicates or a combination of two or more of these. Suitable soluble ingredients for incorporation into seed particles include sodium chloride, potassium chloride, ammonium sulfate, sodium sulfate, sodium sesquicarbonate, urea, citric acid, citrate, sorbitol, mannitol, oleate, sucrose, lactose and the like. Soluble ingredients can be combined with dispersible ingredients such as talc, kaolin or bentonite. Seed particles can be fabricated by a variety of granulation techniques including: crystallization, precipitation, pancoating, fluid-bed coating, fluid-bed agglomeration, rotary atomization, extrusion, prilling, spheronization, drum granulation and/or high shear agglomeration. In the particulates of the present invention, if a seed particle is used, then the ratio of seed particles to particulates is 1:1. Similarly, in the granules of the present invention, the ratio of cores to granules is also 1:1. Preferably, the seed particle delivers acceptable strength while not adversely affecting the density of the final core or granule.

Suitable binders, contemplated for use herein, include common yellow dent starch, modified starches (e.g., hydroxypropyl addition, ethoxylation, acetylation, acid thinning etc.), sugars (e.g., sucrose, dextrose, fructose, lactose etc.), maltodextrin, polyvinylpyrolidine (PVP), polyethylene glycol (PEG), xanthum gum, gum arabic, acacia gum, alginate, carageenan, waxes (e.g., carnuba, beeswax, paraffin and blends thereof), high melting point surfactants (e.g., mp between 40 and 80° C.).

Proteins that are within the scope of the present invention include pharmaceutically important proteins such as hormones or other therapeutic proteins and industrially important proteins such as enzymes.

Any enzyme or combination of enzymes may be used in the present invention. Preferred enzymes include those enzymes capable of hydrolyzing substrates, e.g. stains. These enzymes, which are known as hydrolases, include, but are not limited to, proteases (bacterial, fungal, acid, neutral or alkaline), amylases (alpha or beta), lipases, cellulases and mixtures thereof Particularly preferred enzymes are subtilisins and cellulases. Exemplary subtilisins are described in U.S. Pat. No. 4,760,025, EP Pat. No. 130 756 B1 and PCT Application WO 91/06637, which are incorporated herein by reference. Exemplary cellulases include Multifect L250™ and Puradax™, commercially available from Genencor International. Other enzymes that can be used in the present invention include oxidases, transferases, dehydratases, reductases, hemicellulases and isomerases.

Among the places in the granule where the enzyme can be loaded include: centrally within the low-density material (e.g., in a layer around a centrally located seed particle); intermixed (e.g., homogeneously) with the low-density material; as a layer over, or surrounding, the low-density material; as a layer separated from the low-density material by one or more other layers; as well as any combination thereof.

Suitable plasticizers useful in the present invention include polyols such as glycerol, propylene glycol, polyethylene glycol (e.g., low MW PEGS), urea, or other known plasticizers. Suitable anti-agglomeration agents include fine insoluble or sparingly soluble materials such as talc, $TiO_2$, clays, amorphous silica, magnesium stearate, stearic acid and calcium carbonate. Plasticizers and anti-agglomeration agents can be included, for example, in an overcoating applied to a granule.

As previously mentioned, a barrier layer can be used to slow or prevent the diffusion of substances that can adversely affect the protein or enzyme in the granule. The barrier layer can be made up of a barrier material and can be coated over the core and/or over an enzyme layer that surrounds the core; and/or the barrier material can be included in the core. Suitable barrier materials include, for example, starch, inorganic salts or organic acids or salts. In one embodiment, the barrier layer comprises starch and a binder (e.g., sucrose) coated over a enzyme-containing or carrying, low-density core.

As noted above, the granules of the present invention can comprise one or more coating layers. For example, such coating layers may be one or more intermediate coating layers or such coating layers may be one or more outside coating layers or a combination thereof. Coating layers may serve any of a number of functions in a granule composition, depending on the end use of the enzyme granule. For example, coatings may render the enzyme resistant to oxidation by bleach, prevent enzyme leakage, bring about the desirable rates of dissolution upon introduction of the granule into an aqueous medium, or provide a barrier against ambient moisture in order to enhance the storage stability of the enzyme and reduce the possibility of microbial growth within the granule.

Suitable coatings include water soluble or water dispersible film-forming polymers such as polyvinyl alcohol (PVA), polyvinyl pyrrolidone (PVP), cellulose derivatives such as methylcellulose (MC), hydroxypropyl methylcellulose (HPMC), hydroxyethyl cellulose, carboxymethyl cellulose, hydroxypropyl cellulose, polyethylene glycol, polyethylene oxide, gum arabic, xanthan, carrageenan, chitosan, latex polymers, and enteric coatings. Furthermore, coating agents may be used in conjunction with other active agents of the same or different categories.

Suitable PVAs for incorporation in the coating layer(s) of the granule include partially hydrolyzed, fully hydrolyzed and intermediately hydrolyzed PVAs having low to high degrees of viscosity. Preferably, the outer coating layer comprises partially hydrolyzed PVA having low viscosity. Other vinyl polymers which may be useful include polyvinyl acetate and polyvinyl pyrrolidone. Useful copolymers include, for example, PVA-methylmethacrylate copolymer and PVP-PVA copolymer and enteric co-polymers such as those sold under the tradename Eudragit® (Rhone Poulenc).

The coating layers of the present invention may further comprise one or more of the following: plasticizers, extenders, lubricants, pigments, and optionally additional enzymes. Suitable plasticizers useful in the coating layers of the present invention are plasticizers including, for example, polyols such as sugars, sugar alcohols, or polyethylene glycols (PEGs), urea, glycol, propylene glycol or other known plasticizers such as triethyl citrate, dibutyl or dimethyl phthalate or water. Suitable pigments useful in the coating layers,.of the present invention include, but are not limited to, finely divided whiteners such as titanium dioxide or calcium carbonate or colored pigments and dyes or a combination thereof. Preferably such pigments are low residue pigments upon dissolution. Suitable extenders include sugars such as sucrose or starch hydrolysates such as maltodextrin and corn syrup solids, clays such as kaolin and bentonite and talc. Suitable lubricants include nonionic surfactants such as Neodol, tallow alcohols, fatty acids, fatty acid salts such as magnesium stearate and fatty acid esters.

Adjunct ingredients may be added to the enzyme granules of the present invention. Adjunct ingredients may include: metallic salts; solubilizers; activators; antioxidants; dyes; inhibitors; binders; fragrances; enzyme protecting agents/ scavengers such as ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, proteins such as bovine serum albumin, casein and the like etc.; surfactants including anionic surfactants, ampholytic surfactants, nonionic surfactants, cationic surfactants and long-chain fatty acid salts; builders; alkalis or inorganic electrodlytes; bleaching agents; bluing agents and fluorescent dyes and whiteners; enzyme stabilizers such as betaine, peptides and caking inhibitors.

Preferably, the granules produced in accordance with the present invention are roughly round, or spherical, in shape.

The true, or volumetric, density of the granules can be measured by methods well known in the art, such as by volume displacement using a liquid in which the granules do not dissolve (e.g., mineral oil immersion). Preferably, the granules produced according to the teachings herein have a true density of less than 1.4 $g/cm^3$; more preferably no greater than about 1.2 $g/cm^3$. In one embodiment, the granules have a density of between 0.95–1.4 $g/cm^3$; preferably between about 0.95–1.2 $g/cm^3$; and most preferably between about 1–1.15 $g/cm^3$.

The granules of the present invention may be particularly useful in connection with liquid detergents. In one preferred embodiment, the granules are dispersed and suspended within a liquid detergent having a water content of greater than 50%, and preferably at least about 60%. In one embodiment, the granules have a retained activity in storage for 3 weeks, at 35° C. in such a liquid detergent of at least 50%, and preferably at least 60%, and most preferably at least 70% (e.g., 85% or greater). In another embodiment, the granules have a retained activity in storage for 4 weeks, at 37° C. in such a liquid detergent of at least 50%, and preferably at least 60%, and most preferably at least 70% (e.g., 85% or greater). In yet a further embodiment, the granules have a retained activity in storage under ambient, or normal, storage conditions for 6 months in such a liquid detergent of at least 50%, and preferably at least 60%, and most preferably at least 70% (e.g., 85% or greater).

The granules described herein may be made by methods known to those skilled in the art of particle generation, including but not limited to marumerization, drum granulation, fluid-bed spray-coating, pan-coating, or other suitable process, or combinations of such techniques. Several exemplary methods for producing the particulate compositions and granules of the invention are described next.

In one embodiment, a seed particle is charged into a fluid bed coater and fluidized. A coating solution consisting of a binder or binder system along with a non-porous or minimally porous, low-density material (e.g., hollowspheres) and optionally including other low-density materials is sprayed onto the seed to generate a low density particulate, or core. Also, the non-porous or minimally porous, low-density material (and other low-density materials, if applicable) may be added dry along with application of a binder spray in either a pan or fluidized bed coater. After the core is generated, an enzyme can be layered onto the core. Optionally, this may be followed by other layers whose purpose can be, for example, buffering, providing a protective barrier, bulking, providing another value/performance added material. Finally, a cosmetic coating can be applied to provide aesthetics and protection from the environment. If desired, the entire process can be performed in a pan coater. Moreover, any part of this process can be performed in either a pan coater or a fluidized bed coater.

Suitable seed particles for use in the just-described method include, for example, a sugar crystal, salt crystal, non-pareil, a prill with an acceptable melting point, an extruded particulate, a particulate from a drum granulation, etc.

In another embodiment for forming a granule, a non-porous or minimally porous, low-density material (e.g., hollowspheres) can be blended in a solution consisting of melted components and little or no water or other solvent. This solution can be fed to a spinning disc, centrifugal nozzle or any other type of prilling device which is used to generate spherical particles of sizes between 50 and 3000 um. The prills are generated at some height above a collection area which allows them to cool and harden as they fall. Alternatively, a counter-current chilling air-stream may be used to facilitate prill hardening and control particle velocities. Optionally, enzyme may be added to the hot-melt solution in the form of a dry powder, enzyme-crystal slurry or paste, enzyme precipitate slurry or paste or in a solubilized form in either an aqueous or non-aqueous solvent. In any of the above enzyme additions, solvent of liquid carrier concentration in the hot-melt cannot rise to above a level where spheroidal, non-friable prills are no longer formed. These enzyme prills can then be cosmetically coated, as an option.

In a further embodiment, low-density enzyme granules of the present invention are made by an extrusion method by adding the non-porous or minimally porous, low-density material (e.g., hollowspheres) to the dry blend and then processing as described in, for example, U.S. Pat. No. 5,739,091, incorporated herein by reference.

In yet another embodiment, low-density enzyme granules of the present invention are made by a drum granulation method by adding the non-porous or minimally porous, low-density material (e.g., hollowspheres) to the dry blend and processing as described in, for example, in PCT WO 90/09440, incorporated herein by reference.

In still a further embodiment, the non-porous or minimally porous, low-density material (e.g., hollowspheres) can be blended into a solution/slurry that is used to produce the core of a microencapsulated product. This solution can be sprayed along with a shell solution through a binary phase nozzle, where the core solution exits through the inner liquid port and the shell solution exits through the outer concentric liquid port, and atomized via centrifugal force, mechanical vibration, jet cutting, sonics, cross shear from a liquid or gas stream, electromagnetic field, etc. Depending on the shell, the microencapsulate can be collected in a liquid based collection bath, a solid media that facilitates free-flow of the product or in static or countercurrent air stream that allows hardening/setting up of the product before it reaches a collection vessel. Optionally, the microencapsulate can be dried and/or cosmetically coated.

The shell can be composed of any material(s) that efficiently entrap the inner core and provide enough rigidity so that the microcapsule can be handled in relevant applications without significantly deforming, agglomerating, decomposing or in other ways becoming non-utile.

It should be noted that technologies such as extrusion and drum granulation, where a significant compression force is employed in the production of a granule, might exclude some low density materials if they cannot maintain the low density structure under granulation working pressure. For these technologies, a low density material with a satisfactory pressure/compression tolerance must be employed.

EXAMPLES

The following examples are representative and not intended to be limiting. One skilled in the art could choose other enzymes, fillers, binders, seed particles, methods and coating agents based on the teachings herein.

Example 1

Pan Coated Cores

50 Kgs of non-pareils sieved to between 35 to 40 standard mesh were charged into a 350L pan-coater. The pan was rotated and the product was heated to approximately 50° C. Approximately 1535 grams of sucrose syrup, 62.5% w/w, was sprayed onto the non-pareils until they were sufficiently wet. 432 grams of borosilicate hollowspheres (Q-cel 6042S, produced by PQ Corporation) were added to the pan and dispersed throughout the non-pareils. The pan was allowed to rotate until the non-pareils were sufficiently dry. This method of ingredient addition and drying was repeated 40 more times. After 41 additions, the particles were split into two equivalent coating pans.

To each pan, 1535 grams of sucrose syrup was sprayed. Subsequently, 640 grams of hollowspheres were added. This method of addition was performed 18 times in each pan. Subsequently, 23 more hollowsphere additions were done in each pan by spraying 1535 grams of sucrose syrup and adding 768 grams of hollowspheres for each addition.

After all of the hollowsphere additions were complete, 3 additions of a shellac solution (confectioners glaze) were applied which totaled 2% w/w of the final product.

These low density cores were harvested and classified to between 14 to 25 standard mesh. The final harvest weight was 232 Kgs.

Spray Coating

35 Kgs of the pan-coated low-density cores were loaded into a deseret-60 fluid bed coater and fluidized. To this, 65.8 Kgs of a solution containing 7.3% active alkaline protease and 2.1% polyvinylpyrolidine (Luviskol K-17 from BASF) was spray-coated onto the cores. Subsequently, a 40% solids solution containing 4.8 Kg of dry corn starch, 2.118 Kgs of sucrose and 0.142 Kgs of hydrated starch was spray-coated onto the enzyme particulates. Finally, a cosmetic coating solution containing 3.62 Kgs of hydroxymethyl cellulose (Methocel E from Dow chemical), 4.352 Kgs of titanium dioxide and 0.731 Kgs of polyethylene glycol (PEG 600) was spray-coated on as a final overcoating.

Spray coating Parameters:

| Step | Outlet Temperature (C.) | Fluidized Air Flow (CFM) | Atomization Pressure (PSI) |
|---|---|---|---|
| Core charge | 50 | 1200 | 50 |
| Enzyme spray | 55 | 1800 | 70 |
| Sucrose/starch | 45 | 1800 | 70 |
| Cosmetic coat | 65 | 1800 | 70 |

61.2 Kgs of final product was harvested. The volumetric density determined by mineral oil immersion was 1.18 g/ml Example 2

The following dry ingredients were blended in a Hobard mixer:
a) 600 grams of borosilicate hollowspheres (Q-cel 6042S)
b) 1050 grams of yellow dent corn starch
c) 600 grams of cellulose fibers (Arbosel 600-30)
d) 360 milligrams of lactose
e) 300 grams of high MW polyethylene glycol (PEG 3350 from Dow)
f) 36 grams of low MW polyethylene glycol (PEG 2200 from Dow)
g) 39 grams of polyvinylpyrolidine (Luviskol K-30 from BASF)

To this dry blend, 1615 grams of water was slowly blended in to produce a suitable extrusion dough. The dough was then extruded into strands with a 0.8 mm die. The extruded strands were then marumerized in order to produce roughly spherical particulates.

695 grams of the low density marums were charged into a Vector FL-1 fluidized bed spray-coater and fluidized with 65 CFM of 85° C. fluidizing air. To this, 1710 grams of a 17% w/w total solids solution containing 25 grams of polyvinyl pyrolidine and 1685 grams of a liquid enzyme concentrate containing 7.4% alkaline protease was spray-coated onto the low density marums. Subsequently, 1318 grams of a 25% w/w total solids solution containing 66 grams of lecithin (Ultralec-G from ADM) and 263 grams of yellow dent corn starch was spray coated onto the enzyme marum. Subsequently, 1520 grams of a 13% w/w total solids solution including 82 grams of hydroxypropylmethyl cellulose (Methocel E-15), 99 grams of titanium dioxide and 17 grams of polyethylene glycol (PEG600) was overcoated onto the marums as a cosmetic coating.

1322 grams of product was recovered, with a volumetric density of 1.14 g/ml as determined by mineral oil immersion Example 3

The following dry ingredients were blended in a Hobard mixer:
a) 600 grams of borosilicate hollowspheres (Q-cel 6042S)
b) 1050 grams of yellow dent corn starch
c) 600 grams of cellulose fibers (Arbosel 600-30)
d) 360 milligrams of lactose
e) 300 grams of high MW polyethylene glycol (PEG 3350 from Dow)
f) 36 grams of low MW polyethylene glycol (PEG 2200 from Dow)
g) 39 grams of polyvinylpyrolidine (Luviskol K-30 from BASF)

To this dry blend, 2413 grams of a solution containing 11.4% alkaline protease was slowly blended in to produce a suitable extrusion dough. The dough was then extruded into strands with a 0.8 mm die. The extruded strands were then marumerized in order to produce roughly spherical particulates.

952 grams of the low density enzyme marums were charged into a Vector FL-1 fluidized bed spray-coater and fluidized with 65 CFM of 85° C. fluidizing air. To this, 1318 grams of a 25% w/w total solids solution containing 66 grams of lecithin (Ultralec-G from ADM) and 263 grams of yellow dent corn starch was spray coated onto the enzyme marum. Subsequently, 1520 grams of a 13% w/w total solids solution including 74 grams of hydroxypropylmethyl cellulose (Methocel E-15), 89 grams of titanium dioxide, 20 grams of neodol 23/6.5 (Shell chemical) and 15 grams of polyethylene glycol (PEG600) was overcoated onto the marums as a cosmetic coating.

1378 grams of product was recovered, with a volumetric density of 0.96 g/ml as determined by mineral oil immersion.

Example 4

7.81 Kgs of sucrose seeds, sieved between 35 to 50 standard mesh, were charged into a Glaft GPCG-30 fluidized bed coater, and fluidized with a fluidizing air stream of warm air. To this, 126 Kgs of a 35% w/w total solids solution containing 35 Kgs of an enzyme solution containing 3718 PU/gram alkaline protease, 32 Kgs of yellow dent corn starch, 56.2 Kgs of a solution containing 3.1 Kgs of "cooked out" yellow dent starch, 1.3 Kgs of sucrose, 1.9 Kgs of borosilicate hollowspheres (Q-cel 6048) and 76 grams of 98% formic acid was spray-coated onto the sucrose seeds. Subsequently, 56.3 Kgs of a 13% w/w total solids solution containing 3.3 Kgs hydroxypropylmethyl cellulose (Methocel E-15), 3.3 Kgs titanium dioxide and 0.7 Kgs of polyethylene glycol (PEG 600) was spray coated onto the enzyme particulates as a cosmetic coating.

42.6 Kgs of product was recovered, with 95.7% of the product being larger than 600 um and smaller than 1.18 mm. The activity of the enzyme particulates was 2314 PU/gram. Volumetric density determined by mineral oil immersion was 1.20 g/ml.

Example 6

Analysis of Granules

Stability

In terms of chemical (detergent) stability, granules of the present invention preferably exhibit no more than about 50% loss in activity over 4 weeks storage at 37° C. in detergent and cleaning agents (e.g., dish detergents, laundry detergents, and hot surface cleaning solutions). More preferably, the granules taught herein have a minimum of 70% activity remaining after 4 weeks at 37° C. More preferably still, the granules taught herein have a minimum of 85% activity remaining after 4 weeks at 37° C. In tests carried out in support of the present invention, the granules of Example 1 exhibited nearly 85% activity remaining after 4 weeks at 37° C.

Dust Tests

Two commonly used methods for measuring enzyme granule dust are the Heubach attrition test and the elutriation test. These tests attempt to quantify the tendency of enzyme granules to generate airborne protein aerosols which might potentiate allergic reactions among workers in detergent plants. These tests are designed to reproduce certain mechanical actions typical of handling, conveying and blending operations used to mix enzyme granules into detergents at commercial scale.

In the elutriation test, enzyme granules are placed on a glass frit within a tall glass tube, and fluidized with a constant dry air stream over a fixed time period. In the Heubach attrition test, granules are placed in a small, cylindrical steel chamber fitted with a rotating paddle and steel balls; the granules are pushed around by the paddle and balls, while a dry air stream percolates up through the chamber. In both tests, dust stripped from the particles by the air stream is captured on a glass fiber filter for subsequent weight measurement and activity determination. The elutriation test simulates the removal of surface dust be gentle pouring and fluidizing actions; the Heubach test is a more severe simulation of the crushing forces commonly encountered in industrial powder mixing, conveying, and sieving operations. Additional details of these tests can be found, for example, in "Enzymes In Detergency," ed. Jan H. van Ee, et al., Chpt. 15, pgs. 310–312 (Marcel Dekker, Inc., New York, N.Y. (1997)), and references cited therein.

Granules of the present invention preferably exhibit a dust figure of less than 1 ug/g (active dust) as determined by the elutriation attrition test. Exemplary granules that have been tested in support of the present invention exhibit a dust figure of no greater than 1 ug/g.

Enzyme Release

A commonly used method for measuring enzyme release from a granule under typical liquid applications conditions is the enzyme dissolution test. In this test, granules are added to a liquor that is chemically equivalent to the application conditions. The test liquor can be set at differing temperatures to test for different application temperatures. The granule containing liquor is agitated under conditions that are similar to application conditions, and samples of particulate-free liquor are removed with a filtered syringe at various times. The samples are then assayed for enzyme activity (e.g., for proteases, by way of a standard assay involving the hydrolysis of casein substrate).

Granules of the present invention preferably have at least 80%, and preferably at least 90%, of the enzyme activity released into the liquor within 5 minutes at 15° C. More preferably, the granules taught herein have a minimum of 90% of the enzyme activity released into the liquor within 3 minutes at 15° C. Exemplary granules that have been tested in support of the present invention exhibit an enzyme release rate of no less than 90% in 5 minutes at 15° C, and most exhibit an enzyme release rate of no less than 90% in 3 minutes at 15° C.

Summary Table

| Granule Sample | Volumetric Density (g/ml) |
|---|---|
| Example 1 | 1.18 |
| Example 2 | 1.14 |
| Example 3 | 0.96 |
| Example 4 | 1.20 |

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

It is claimed:

1. A low-density composition including a non-porous or minimally porous, low-density material, a binder, and an enzyme, the composition having a specific gravity less than 1.2 g/cm$^3$.

2. The composition of claim 1, wherein the non-porous or minimally porous, low-density material is selected from the group consisting of hollowspheres, low-density minerals that are minimally soluble and minimally porous in water, low-density wood materials, and any mixture thereof.

3. The composition of claim 2, wherein the non-porous or minimally porous, low-density material is comprised of hollowspheres.

4. The composition of claim 1, having a specific gravity of between 0.95 and 1.15 g/cm$^3$.

5. An enzyme core for enzyme granules, comprising (i) a low-density composition including (a) a non-porous or minimally porous, low-density material and (b) a binder; and (ii) an enzyme enrobing said composition, the enzyme core having a specific gravity less than 1.2 g/cm$^3$.

6. The enzyme core of claim 5, wherein the non-porous or minimally porous, low-density material is selected from the group consisting of hollowspheres, low-density minerals that are minimally soluble and minimally porous in water, low-density wood materials, and any mixture thereof.

7. The enzyme core of claim 6, wherein the non-porous or minimally porous, low-density material is comprised of hollowspheres.

8. The enzyme core of claim 5, wherein the low-density composition is substantially free of enzymes therein.

9. The enzyme core of claim 5, having a specific gravity of between 0.95 and 1.15 g/cm$^3$.

10. The low-density composition of claim 1 further comprising an outer coating.

11. The low-density composition of claim 10 wherein the non-porous or minimally porous, low-density material is selected from the group consisting of hollowspheres, low-density minerals that are minimally soluble and minimally porous in water, low-density wood materials, and any mixture thereof.

12. The low-density composition of claim 11 wherein the non-porous or minimally porous, low-density material is comprised of hollowspheres.

13. The low-density composition of claim 12 wherein the hollowspheres are borosilicate glass hollowspheres.

14. The low-density composition of claim 10 having, a specific gravity of 0.95 –1.15g/cm$^3$.

15. The enzyme core of claim 5 further comprising an outer coating.

16. The enzyme core of claim 15 wherein the non-porous or minimally porous, low-density material is selected from the group consisting of hollowspheres, low-density minerals that are minimally soluble and minimally porous in water, low-density wood materials, and any mixture thereof.

17. The enzyme core of claim 16 wherein the non-porous or minimally porous, low-density material is comprised of hollowspheres.

18. The enzyme core of claim 17 wherein the hollowspheres are borosilicate glass hollowspheres.

19. The enzyme core of claim 15 having a specific gravity of 0.95–1.15 g/cm$^3$.

\* \* \* \* \*